United States Patent
Mazur et al.

[11] 4,407,746
[45] Oct. 4, 1983

[54] CYCLOHEXYL AND PHENYL SUBSTITUTED ENKEPHALINS

[75] Inventors: Robert H. Mazur, Chicago; David A. Tyner, Glenview; Eleanor A. Hallinan, Evanston, all of Ill.

[73] Assignee: G. D. Searle & Co., Skokie, Ill.

[21] Appl. No.: 330,614

[22] Filed: Dec. 14, 1981

[51] Int. Cl.³ .................... C07C 103/52; A61K 37/00
[52] U.S. Cl. ............................. 260/112.5 E; 424/177
[58] Field of Search ................. 260/112.5 R, 112.5 E; 424/177

[56] References Cited

U.S. PATENT DOCUMENTS

| | | | |
|---|---|---|---|
| 4,261,883 | 4/1981 | Smolarsky | 260/112.5 E |
| 4,309,343 | 1/1982 | Gesellchen | 260/112.5 E |
| 4,331,593 | 5/1982 | Smithwick, Jr. et al. | 260/112.5 E |
| 4,350,627 | 9/1982 | de Castiglioni et al. | 260/112.5 R |

OTHER PUBLICATIONS

Biological Abstracts (1980), vol. 69, p. 12570.

*Primary Examiner*—Delbert R. Phillips
*Attorney, Agent, or Firm*—James G. Passe

[57] ABSTRACT

The invention discloses cyclohexyl and phenyl substituted enkephalin derivatives of the formula:

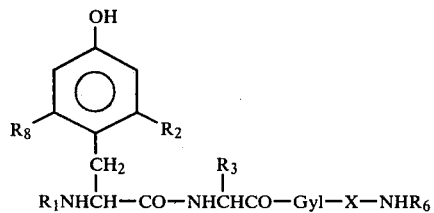

Where $R_1$, $R_2$, $R_4$, and $R_8$ is hydrogen or alkyl of $R_3$ is alkylthioalkyl or alkylsulfinylalkyl, X is:

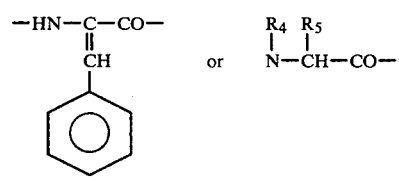

$R_5$ is cyclohexylmethyl, phenylmethyl, optionally substituted by —$NO_2$, $R_6$ is cyclohexyl or phenyl optionally substituted by $R_7$ and $R_7$ is hydrogen, an alkyl ester of carboxylic acid or hydroxyalkyl and the pharmaceutically acceptable salts, which are useful as analgesic agents.

9 Claims, No Drawings

CYCLOHEXYL AND PHENYL SUBSTITUTED ENKEPHALINS

BACKGROUND OF THE INVENTION

The present invention relates to novel enkephalin derivatives. In particular, it provides novel enkephalin derivatives of formula I which are useful as analgesic agents.

In 1975, a pentapeptide, methionine enkephalin, was reported by Hughes et. al. Nature, 258, p.577 (1975). This peptide is found in many areas of the brain where it appears to act as a neurotransmitter or neuromodulator in a central painsuppressant system. The natural peptide binds sterospecifically to partially purified brain opiate receptor sites, see for example, Bradberry et. al., Nature 260, p.793 (1976). The natural peptide is also highly active in bioassays for opiate activity but exhibits only weak, fleeting analgesic activity when injected directly into the brain of the rat, see for example, Belluzi et. al., Nature, 260, 625 (1976).

In order to overcome the lack of in vivo activity, a number of investigators have made numerous modifications in the methionine enkephalin structure, such as substituting the glycine in the 2-position with a D-amino acid, N-methylation of the 1-tyrosine; substituting the 4-phenylalanine with, for example, methyl or halo; modifying the C-terminus, etc. to produce enkephalin derivatives of varying properties and potencies. The present invention provides new enkephalin derivatives which approach the potency of morphine as analgesic agents by both oral and parenteral routes of administration.

SUMMARY OF THE INVENTION

The present invention particularly provides enkephalin derivatives according to Formula I:

wherein $R_1$ is:
(a) hydrogen; or
(b) alkyl of 1 to 6 carbon atoms, inclusive;
wherein $R_2$ and $R_8$ are:
(a) hydrogen; or
(b) alkyl of 1 to 6 carbon atoms, inclusive; $R_2$ and $R_8$ each being the same or different;
wherein $R_3$ is:
(a) alkyl of 1 to 6 carbon atoms, inclusive;
(b) —$C_4H_9$;
(c) alkylthioalkyl, having 2 to 6 carbon atoms, inclusive;
(d) alkylsulfinylalkyl, having 2 to 6 carbon atoms inclusive; or
(e) alkoxyalkyl, having 2 to 6 carbon atoms inclusive;
wherein X is:

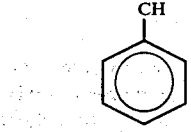

wherein $R_4$ is:
(a) hydrogen; or
(b) alkyl of 1 to 6 carbon atoms, inclusive;
wherein $R_5$ is:

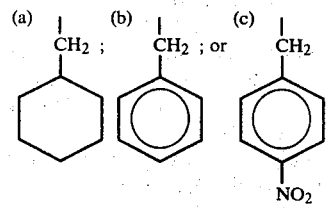

wherein $R_6$ is:
(a) cyclohexyl; substituted 2, 3, or 4 by $R_7$; or
(b) phenyl; substituted ortho, meta or para by $R_7$;
wherein $R_7$ is:
(a) hydrogen;
(b) $CO_2$-alkyl having 1 to 6 carbon atoms inclusive; or
(c) hydroxy alkyl of one to six carbon atoms inclusive.

Examples of alkyl of one to six carbon atoms inclusive, are methyl, ethyl, propyl, butyl, pentyl and hexyl and the isomeric forms thereof.

The analgesic activity for the compounds of the present invention was established in the hot-plate assay and mouse PBQ-writhing assay, and the analgesic activity of the representative compounds was compared with that of morphine.

Hot-plate assay. Male CRL: COBS CD-1 (1CR) BR mice weighing 20 to 30 grams are used. Two groups of 14 mice are brought into the experiment room approximately one-half hour prior to testing. The mice are placed individually in a restraining cylinder placed on a hot plate with temperature controlled by a proportional temperature controller at 55 degrees plus or minus 0.5 degrees centigrade. The reaction time of each mouse to lick a foot or jump is measured 3 times at 20 minute intervals. Mice not responding within 15 seconds are discarded. Ten mice are given a dose of the test drug and ten are given 0.9 percent saline, containing approximately 0.09 ml's of a 50/50 mixture of propylene glycol and polysorbate 80, intraveneously 20 minutes after the last reaction time measurement. The animals are tested as before 10, 30 and 60 seconds after this injection. Mice not responding within 30 seconds are removed from the hot plate and given a response time of 30 seconds. Analgesia is considered to be demonstrated in the mouse if its post drug reaction time is greater than that of the control mean plus two standard deviations. The number of animals showing analgesia in the drug group is compared with that same value for the control group by means of Fisher's exact probability test. The $ED_{50}$ is then calculated. Eddy, N. B. et al. synthetic analgesics, National Institute of Arthritis and Metabolic Diseases, National Institute of Health Bethesda, Md., pages 385–393, 1952 and Siegal, S: Non-parametrics statistics for the behavioral sciences, New York: McGraw Hill Book Company, 1956.

PBQ-Writhing assay. Groups of 10 male mice weighing 20 to 35 grams are used for each dose and for the vehicle control. Writhing is induced 30 or 60 minutes following drug or drug vehicle administration by the IP injection of a 0.025 percent solution of PBQ and 5 percent ethanol. The number of separate writhing motions occuring in a ten minute period starting 5 minutes following the PBQ challenge is counted for each mouse. A positive antinociceptive affect is assured when an individual animal's writhing frequency is less than or equal to 50 percent of the vehicle control group median frequency. ED$_{50}$ values based on the number of positive responders per dose group is determined using the method of Litchfield and Wilcoxon. M. R. Fennessy et al. The assessment of and problems involved in the experimental evaluation of narcotic analgesics. In methods in narcotics research. Marcel Dekker, Inc., New York, 1975 H. Bomberg et al. use of writhing test for evaluating analgesic activity of narcotic analgesics, Proc. Soc. Ext. Biol. Med. 118: 763–766, 1965. These tests show that the novel compounds are useful as analgesic agents in the dosage ranges about 0.1 to 100 milligrams per kilogram.

By virtue of the analgesic activity, the compounds of Formula I are useful in treating pain in humans and animals. A physician or veterinarian of ordinary skill could readily determine a subject who is exhibiting such pain. Regardless of the route of administration selected, the compounds of the present invention are formulated into pharmaceutically acceptable dosage forms by conventional methods known to the pharmaceutical art. The compounds can be administered in such oral dosage forms as tablets, capsules, pills, powders, granules, suspensions, or solutions. They may also be administered rectally or vaginally, in such forms as suppositories, creams or ointments. They may also be introduced in the form of eyedrops, interparenterally, subcutaneously, or intramuscularly, using forms known to the pharmaceutical art. In general, the preferred form of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal; the severity of the symptoms; and the route of administration of the particular compound employed. An ordinary skilled physician or veterinarian will readily determine and prescribe the effective amount, based on the route of administration of the analgesic agent, to prevent or arrest the progress of the condition. In so proceeding, the physician or veterinarian could employ relatively low dosages at first, subsequently increasing the dose until a maximum response is obtained.

The compounds of Formula I can also be administered as pharmacologically acceptable acid addition salts such as the hydrochloride, hydrobromide, hydroiodide, sulfate, phosphate, acetate, propionate, lactate, maleate, malate, succinate, tartrate, and the like. Additionally, the compounds of this invention may be administered in a suitable hydrated form.

The compounds of this invention are prepared by a "block-type" synthesis in which multi-residue peptide units are preformed and then combined covalently to give the oligopeptide product. See Charts which follow. The method described herein uses units composed of three amino acids for the amino terminal moiety and two amino acids for the carboxy terminal moiety, such that the product contains a modified amino acid analog at the carboxyl terminus. An α-D-amino acid, after suitable protection of the α-amino group and other reactive centers, is activated for coupling by conversion to a mixed anhydride intermediate using a hindered alkyl chloroformate. Reaction with glycine methyl ester provides a protected intermediate peptide, from which the amino protecting group is then removed. Tyrosine or a substituted derivative of tyrosine, after suitable protection of the α-amino group and activation as a mixed anhydride, is coupled with the intermediate dipeptide ester. Hydrolysis of the ester provides the tripeptide unit in the free carboxylic acid form for coupling with the dipeptide unit. Phenylalanine or an analog thereof, after suitable protection of the α-amino group and activation as a mixed anhydride, is coupled with the methyl ester of a modified amino acid analog, affording the other peptide unit as a protected derivative. Removal of the amino protecting group provides the dipeptide unit in the amino form for coupling with the tripeptide unit. The tripeptide unit is activated by conversion to the mixed anhydride intermediate and is coupled with the dipeptide unit. Removal of the amino protecting groups from the product affords the oligopeptide compounds of this invention.

The invention will appear more fully from the examples which follow. These examples are given by way of illustration only and are not to be construed as limiting the invention either in spirit or in scope, as many modifications both in materials and in methods will be apparent from this disclosure to those skilled in the art.

EXAMPLE 1

Boc-D-Met-Gly-OMe

N-t-butoxycarbonyl-D-methionine (24.9 g, 0.1 mole) is dissolved in 125 ml DMF and 11.2 ml (0.1 mole) N-methylmorpholine is added. The solution is cooled to −50° and 13.2 ml (0.1 mole) isobutyl chloroformate is added dropwise with stirring. The mixture is warmed to −15° and cooled again to −50°. Glycine methyl ester hydrochloride (13.8 g; 0.11 mole) is added followed by 12.3 ml of N-methylmorphine. The mixture is stirred overnight at room temperature.

The mixture is poured into 1 liter of ethyl acetate. The ethyl acetate is washed with water, 0.5 M potassium bisulfate, and 0.5 M potassium bicarbonate, dried over magnesium sulfate, and taken to dryness under vacuum. The solid residue was crystallized from ethyl acetate-hexane to give the title dipeptide 27.1 g (85 percent), having a melting point of 87°–90° C. The NMR spectrum was consistent with the structure.

EXAMPLE 2

D-Met-Gly-OMe HCl

The product of Example 1 is dissolved in 290 ml of dioxane and 145 ml of 5.6 M hydrogen chloride in dioxane added with stirring. After one hour at room temperature, tlc (10 percent methanol-chloroform) show complete deblocking. The solution is taken to dryness under the vacuum and the gummy residue shaken with ether to remove dioxane and excess hydrogen chloride. The ether is decanted and the product dried under high vacuum. The NMR spectrum agreed with the structure for the title compound. The dipeptide ester salt is a hygroscopic glass and is used immediately.

EXAMPLE 3

Boc-Tyr-D-Met-Gly-OMe

N-t-Butoxycarbonyl tyrosine (23.8 g., 84 mmoles) is dissolved in 150 ml. of 2:1 methylene chloride-tetrahydrofuran and 9.3 ml. (84 mmoles) N-methylmorpholine added. The solution is cooled to −50° and 11.1 ml. (84 mmoles) isobutyl chloroformate added dropwise with stirring. The mixture is warmed to −15° and cooled again to −50°. D-Met-Gly-OMe.HCl (21.7 g., 84 mmoles) in 150 ml 2:1 methylene chloride-tetrahydrofuran is added followed by 9.3 ml. (84 mmoles) of N-methylmorpholine. The mixture is stored overnight at room temperature.

The reaction mixture is washed with 1 M potassium bisufate (3 times), saturated potassium carbonate (2 times) and saturated NaCl. The organic layer is dried over sodium sulfate, the drying agent removed, and the filtrate concentrated to dryness under reduced pressure.

The crude product is reprecipitated from ethyl acetatehexane to give a powder, 29.4 g. (72 percent), homogeneous on tlc (5 percent methanol-chloroform). The NMR spectrum agreed with the structure of the title tripeptide.

EXAMPLE 4

Boc-Tyr-D-Met-Gly

The title compound of Example 3 (12.6 g., 26 mmoles) is dissolved in 78 ml. of methanol and 78 ml of 1 N sodium hydroxide is added dropwise with stirring to give a clear solution. After ½ hour, the tlc (5 percent methanol-chloroform) showed that saponification was complete.

The solution is concentrated under vacuuum to remove methanol, washed with ether to remove any neutral impurities, and acidified to pH 3 with 2 M potassium bisulfate. The oily product is shaken with fresh water until crystallization is complete. The product is then filtered and washed with a large volume of water and a large volume of ether. The yield of pure material was 9.98 g (81 percent). The NMR spectrum agrees with the structure, for the title compounds.

EXAMPLE 5

Boc-Tyr-D-Met-Gly-Phe-DL-cis-3-aminocyclohexanecarboxylic Acid Methyl Ester and Boc-Tyr-D-Met(O)-Gly-Phe-DL-cis-3-aminocyclohexanecarboxylic Acid Methyl Ester The title compound of Example 4 (1.69 g. 3.6 mmoles) is dissolved in 40 ml tetrahydrofuran plus 4 ml dimethylformamide. N-Methylmorpholine (0.4 ml, 3.6 mmoles) is added and the solution cooled to −50°. Isobutyl chloroformate (0.47 ml, 3.6 mmdes) is added with stirring and the mixture warmed to −15° C., the mixture is then cooled to −50° C. Phe-DL-3-cis-aminocyclohexanecarboxylic acid methyl ester-HCl (cis) (1.21 g., 3.6 mmoles) is added followed by 0.4 ml. N-methylmorpholine. The mixture was stirred overnight at room temperature. Ethylacetate is added and the mixture washed with potassium bisulfate (3 times), saturated potassium carbonate (3 times) and saturated NaCl (2 times). The organic layer is dried over sodium sulfate and the solvent removed under vacuum. The residue (2.3 g.) consisted of two products.

The crude material is chromatographed on Woelm silica and eluted with methanol-chloroform (1 percent, 2 percent, 5 percent). The less polar product is the methionine pentapeptide, title compound yield 1.11 g. The more polar product is the methionine sulfoxide pentapeptide, title compound yield 0.90 g. NMR spectra clearly confirmed the structures of these substances.

EXAMPLE 6

Tyr-D-Met-Gly-Phe-DL-cis-3-aminocyclohexanecarboxylic Acid Methyl Ester HCl

The title compound of Example 5 methionine pentapeptide (1.10 g., 1.5 mmoles) is dissolved in 1 ml of acetic acid and 2.5 ml 5.6 M hydrogen chloride in dioxane is added. After ½ hour at room temperature, the solvents are removed under vacuum. The residue is rubbed with ether to give a white powder, 0.95 g (91 percent), homogeneous on tlc (30 percent methanol-chloroform). The NMR spectrum is consistent with the title compound.

EXAMPLE 7

Tyr-D-Met(O)-Gly-Phe-DL-cis-3-aminocyclohexanecarboxylic Acid Methyl Ester HCl

The methionine sulfoxide pentapeptide (0.89 g., 1.2 mmoles) is dissolved in 4 ml. of acetic acid and 2 ml. of 5.6 M hydrogen chloride in dioxane is added. After ½ hour at room temperature, the solution is taken to dryness under vacuum and the residue triturated with ether. It was shown by tlc (30 percent methanol-chloroform) that partial conversion of methionine sulfoxide to methionine had taken place.

The total product is dissolved in 3 ml of methanol-water (2:1) and treated with 0.5 ml. 10 M hydrogen peroxide. After one hour, 100 ml of water is added and the solution lyophilized. The fluffy product, 0.77 g (91 percent), was now homogeneous on tlc (30 percent methanol-chloroform) and NMR showed the title product.

EXAMPLE 8

D,L-cis-3-aminocyclohexanecarboxylic Acid

3-Aminobenzoic acid (25 g, 0.18 mole) in 475 ml of water is hydrogenated at 125° C. over 2.5 g of 5 percent ruthenium on charcoal using hydrogen at 1400 psi pressure. After uptake of hydrogen is complete, catalyst is removed by filtration, and the filtrate is concentrated in vacuo at 60° C. to a solid residue. The crude product is stirred with ethanol, collected, and washed with ethanol. Drying in a vacuum oven at 60° gave 21 g (0.15 mole) of the title product, having a melting point of 288°–294° C. with decomposition. Mixed melting with a sample prepared from the known lactam (which can only be cis) showed no depression of melting point.

EXAMPLE 9

D,L-cis-3-aminocyclohexanecarboxylic Acid Methyl Ester Hydrochloride

To 280 ml of cold methanol is slowly added 20 ml (0.28 mole) of thionyl chloride, followed by 20 g (0.14 mole) of D,L-cis-3-aminocyclohexanecarboxylic acid. After being heated at reflux for 2 hr., the solution is allowed to cool and stand for 12 to 24 hours at ambient temperature. The solution is concentrated in vacuo to an oil which is crystallized from methanol and diethyl ether. The crystals are filtered, washed with diethyl ether, and dried over potassium hydroxide in a vacuum desiccator, giving slightly impure product. Recrystallization from acetone gives 11.5 g (0.07 mole) of the title products as crystals which, after collecting and drying in vacuum as before, is analytically pure. Structure assignment is supported by the NMR spectrum and elemental analysis (C,H,N,Cl).

EXAMPLE 10

Boc-Phe-DL-cis-3-aminocyclohexanecarboxylic Acid Methyl Ester

N-t-Butoxycarbonyl-L-phenylalanine (6.9 g, 0.026 mole) and N-methylmorpholine (5.3 g, 0.052 mole) are stirred in 40 ml of dry dichloromethane, cooled to −50° to −60°. Isobutyl chloroformate (3.6 g, 0.026 mole) is added dropwise, and the mixture is allowed to warm to 0°. After 30 minutes, the mixture is again cooled to −50°. DL-cis-3-aminocyclohexanecarboxylic acid methyl ester hydrochloride (4.0 g, 0.026 mole) in 40 ml of dry dichloromethane is added, and the reaction mixture is allowed to warm to room temperature and is stirred for 12 to 24 hours. The mixture is washed with 2 M potassium carbonate (two times, total of 50 ml), 1 M potassium bisulfate (two times, total of 50 ml), and saturated NaCl solution. The organic layer is dried over sodium sulfate, filtered, and concentrated to dryness under reduced pressure. Drying at 70° under vacuum produces 7.7 g (0.019 mole of the title product as a tan solid. Structure assignment is supported by the NMR spectrum and elemental analysis (C,H,N).

EXAMPLE 11

Phe-cis-3-aminocyclohexanecarboxylic Acid Methyl Ester HCl

The title compound of Example 10 (2.00 g., 4.9 mmoles) was dissolved in 22 ml. of glacial acetic acid and 11 ml. of 5.6 M hydrogen chloride in dioxane is added. After ½ hour at room temperature, the solution is concentrated to dryness under vacuum. The gummy residue resists all attempts to make it solidify. Finally, the title product is dried under high vacuum at 55°. The yield is quantitative. Tlc (methylene chloride-methanol-conc. ammonium hydroxide 85:14:1) showed the substance to be nearly homogeneous and NMR confirmed the structure.

EXAMPLE 12

Methyl-3-aminobenzoate Hydrochloride

The title compound is prepared according to the method of Example 9 using 13.7 g (0.1 mole) of m-aminobenzoic acid, 250 ml of methanol, and 21.9 ml (0.29 mole) of thionyl chloride, except that the mixture is not heated. After concentration of reduced pressure, the product is shaken with diethyl ether, producing 18.7 g (0.10 mole) of crystalline solid. Structure is confirmed by NMR spectrum.

EXAMPLE 13

N-Carbobenzyloxyphenylalanyl-cis-3-aminobenzenecarboxylic Acid Methyl Ester

The title compound is prepared according to the method of Example 10 using 2.99 g (0.01 mole) of N-carbobenzyloxyphenylalanine in 25 ml of dichloromethane, 2.24 g (0.02 mole of N-methylmorpholine, 1.32 ml (0.01 mole of isobutyl chloroformate, and 1.88 g (0.01 mole of methyl 3-aminobenzoate hydrochloride in 10 ml of dichloromethane. After extracting according to Example 10, analytically pure title product is crystallized from 40 ml of isopropyl alcohol as needles (3.0 g, 0.0069 mole) having a melting point of 156°–159° C. Structure assignment is supported by elemental analysis (C,H,N).

EXAMPLE 14

Phe-3-aminobenzenecarboxylic Acid Methyl Ester HBr

The title product of Example 13 (3.00 g, 6.9 mmoles) dissolved in 13.5 ml of warm acetic acid is treated with 13.5 ml of 5.1 N HBr in acetic acid for 2 hours. Solvent is removed at reduced pressure, and the residue is triturated with diethyl ether and collected by filtration. The resultant solid is washed well with diethyl ether and dried by warming gently in open air, giving 2.66 g (6.9 mmole) of the title product. Structure assignment is supported by elemental analysis (C,H,N,Br).

EXAMPLE 15

Boc-Tyr-D-Met-Gly-Phe-cis-3-aminobenzenecarboxylic Acid Methyl Ester

The title compound is prepared according to the method of Example 5 using 1.23 g (2.6 mmole) of Boc-Tyr-D-Met-Gly (from Example 4) in 10 ml of dichloromethane and 5 ml of dimethylformamide, 0.57 ml (5.2 mmole) of N-methylmorpholine, 0.34 ml (2.6 mmoles) of isobutylchloroformate, and 1.00 g (2.6 mmole) of title compound of Example 12 (from Ex. 12.). After extracting according to Example 5, analytically pure product (1.68 g., 2.2 mmoles) is isolated as the monohydrate by stripping solvent at reduced pressure. Structure assignment is supported by elemental analysis (C,H,N,S).

EXAMPLE 16

Tyr-D-Met-Gly-Phe-3-aminobenzenecarboxylic Acid Methyl Ester HCl

The title compound is prepared according to the method of Example 6 using 1.60 g (2.1 mmole) of the Boc-protected pentapeptide (from Example 15) in 7.2 ml of acetic acid, and 3.6 ml of 5.6 N HCl in dioxane. After 5 minutes, solvent is removed under reduced pressure, and the residue is triturated with diethyl ether, giving 1.35 g (1.9 mmole) of the title product as the monohydrate. Structure assignment is supported by elemental analysis (C,H,N,S).

EXAMPLE 17

N-t-Butyloxycarbonyl-Phenylalanyl-3-aminobenzyl Alcohol

N-t-butyloxycarbonylphenylalanine (1.00 g, 3.8 mmole) is dissolved in 4 ml of dichloromethane, in which is then suspended m-aminobenzyl alcohol. The cooled mixture is treated with 0.78 g (3.8 mmole) of dicyclohexylcarbodiimide for 12 to 24 hours. Dicyclohexylurea is removed by filtration, using an ethyl acetate wash. The filtrate is extracted three times with saturated aqueous potassium bisulfate, three times with aqueous potassium bicarbonate, and once with brine. The organic layer is dried over magnesium sulfate, filtered, and blown dry under flowing nitrogen. Column chromatography using silica gel and chloroform eluent produces, after removal of solvent, 1.19 g (3.2 mmole) of pure product. Structure assignment is supported by elemental analysis (C,H,N).

EXAMPLE 18

Phenylalanyl-3-aminobenzyl Alcohol HCl

The title compound is prepared according to the method of Example 11 using 1.09 g (2.9 mmole) of the title compound from Ex. 17 in 10 ml of dioxane, and 5 ml of 5.6 N HCl in dioxane for 10 min. After stripping the solvent the crude product is triturated with diethyl ether. The solid is redissolved in dioxane and forced out with diethyl ether, giving 0.68 g (2.2 mmole) of product as the monohydrate. Structure assignment is supported by elemental analysis (C,H,N,Cl).

EXAMPLE 19

N-t-Butyloxycarbonyl-N-methyltyrosine

N-t-Butyloxycarbonyl-O-benzyltyrosine (37.1 g, 0.10 mole) and 50 ml (0.81 mole) of methyl iodide are dissolved in 300 ml of tetrahydrofuran and cooled in an ice bath. Batches of sodium hydride, as a 50-percent oil dispersion, are added until a total of 14.4 g (0.30 mole) is used. After 1 day, the cold reaction is allowed to warm to room temperature and is stirred for an additional day. The reaction is quenched with 6 ml of water and concentrated nearly to dryness at reduced pressure. A solution in 200 ml of water is adjusted to pH 2 with saturated potassium bisulfate and extracted with 250 ml of ethyl acetate. The organic phase is washed successively with water, aqueous potassium bicarbonate, and water, and dried over magnesium sulfate. After removal of solvent, the N-methylated intermediate is recrystallized from toluene, giving 26.1 g (0.068 mole) of analytically pure solid (by C,H,N analyses).

A portion (25.8 g, 0.067 mole) of the intermediate is hydrogenolyzed in methanol at 60 psi over palladium black until cessation of hydrogen uptake. Insolubles are removed by filtration, and the solvent is removed, giving 5.6 g (0.019 mole) of N-t-butyloxycarbonyl-N-methyltyrosine. Structure assignment is supported by elemental analysis (C,H,N).

EXAMPLE 20

N-t-Butyloxycarbonyl-N-methyl-Tyr-D-Met-Gly

The title compound is prepared according to the methods of Example 3 and Example 4 using 5.6 g (0.019 mole) of N-t-butoxycarbonyl-N-methyltyrosine in 30 ml of methylene chloride and 15 ml of tetrahydrofuran, 4.2 ml (0.038 mole) of N-methylmorpholine, 2.50 ml (0.019 mole) of isobutylchloroformate, and 4.9 gm (0.019 mole) of D-Met-Gly-OMe.HCl in 30 ml of methylene chloride and 15 ml of tetrahydrofuran. Extraction and drying in vacuo gives the peptide ester (6.1 g, 0.012 mole). The ester is hydrolyzed in one hour using 36 ml of 1 N sodium hydroxide in 36 ml of dioxane. Neutralization, extraction, and concentration to dryness gives 5.9 g (0.012 mole) of product, pure by analysis (C,H,N,S).

EXAMPLE 21

N-t-Butyloxycarbonyl-N-methyl-Tyr-D-Met-Gly-Phe-3-aminobenzyl Alcohol

The title compound is prepared according to the method of Example 5 using 1.06 g (2.2 mmole) of Boc-Tyr-D-Met-Gly (from Ex. 20) in 10 ml of dichloromethane, 0.24 ml (2.2 mmole) of N-methylmorpholine, 0.29 ml (2.2 mmole) of isobutyl chloroformate, and 0.67 g (2.2 mmole) Phe-3-aminobenzyl alcohol in 10 ml of dichloromethane. Purification is effected by column chromatography on silica gel using dichloromethane as eluent. The intermediate product (1.18 g, 1.6 mmole) is used in subsequent deblocking process without further purification.

EXAMPLE 22

N-Methyl-Tyr-D-Met-Gly-Phe-3-aminobenzyl Alcohol HCl

The title compound is prepared according to the method of Example 6 using 0.38 g (0.52 mmole) of the N-t-butyloxycarbonyl-protected pentapeptide (from Ex. 21) in 5 ml of dioxane, and 2.5 ml of 5.6 N HCl in dioxane. After 5 minutes, solvent is removed under reduced pressure and the residue is titurated with diethyl ether. The solid is redissolved in methanol and forced out with diethyl ether, giving 0.33 g (0.49 mmole) of product as the monohydrate. Structure assignment is supported by elemental analysis.

EXAMPLE 23

N-t-Butyloxycarbonyl-N-methylphenylalanyl-cis-3-aminocyclohexanecarboxlic Acid Methyl Ester The title compound is prepared according to the method of Example 10 using 0.28 g (1.0 mmole) of N-t-butyloxycarbonyl-N-methylphenylalanine in 5 ml of dichloromethane, 0.22 ml (2.0 mmole) of N-methylmorpholine, 0.14 ml (1.0 mmole) of isobutyl chloroformate, and 0.19 g (1.0 mmole) of DL-cis-3-amino-cyclohexylcarboxylic acid methyl ester hydrochloride. After extracting according to Ex. 10 0.41 g (1.0 mmole) product is recovered by concentrating to dryness in vacuo. Structure assignment is supported by NMR and elemental analysis (C,H,N).

EXAMPLE 24

N-Methylphenylalanyl-cis-3-aminocyclohexanecarboxylic Acid Methyl Ester HCl

The title compound is prepared according to the method of Example 11 using 0.34 g (0.81 mmole) of the title compound of Example 23 in 5 ml of dioxane, and 2.5 ml of 5.6 N HCl in dioxane for 15 min. Solvent is stripped and the residue is triturated with diethyl ether. The solid is redissolved in methanol and forced out with diethyl ether, giving quantitative recovery of very hygroscopic solid. The product is used in subsequent synthesis without further purification.

EXAMPLE 25

N-t-Butyloxycarbonyl-DL-2,6-dimethyl Tyr-D-Met-Gly-N-methyl-Phe-DL-cis-3-aminocyclohexanecarboxylic Acid Methyl Ester The title compound is prepared according to the method of Example 5 using 0.40 g (0.80 mmole) of N-methylmorpholine, 0.11 ml (0.84 mmole) of isobutylchloroformate, and 0.28 g (0.79 mmole) of the title compound of Example 24. After extraction and concentration at reduced pressure, the crude product is purified by chromatography on silica gel using chloroform with slowly increasing fraction of methanol (from 1 percent to 5 percent by volume). Two isomers of the Boc-protected pentapeptide product are isolated as indicated by the NMR spectra, one component being the isomer with D-stereochemistry in the 2,6-dimethyl-tyrosine residue, and the other being the L-isomer. The t-butyloxycarbonyl protecting group is removed from both isomers before further characterization.

EXAMPLE 26

(D or L)-2,6-Dimethyl-Tyr-D-Met-Gly-N-methyl-Phe-DL-cis-3-aminocyclohexanecarboxylic Acid Methyl Ester HCl (Isomer A)

The title compound (Isomer A) is prepared according to the method of Example 6 using 0.098 g (0.12 mmole) of the first eluted product pentapeptide from Example 25 in 1 ml of acetic acid, and 1 ml of 5.6 N HCl in dioxane. The solution is concentrated at reduced pressure after 15 minutes and the residue is taken up in methanol and redried. The residue is triturated in 1:1 ethyl acetate and Skellysolve B and collected, giving 0.052 g (0.007 mmole) of Isomer A as the sesquihydrate. Structure assignment, except for D or L stereochemistry of the 2,6-dimethyltyrosine residue, is confirmed by NMR and elemental analysis (C,H,N,Cl).

EXAMPLE 27

(L or D)-2,6-Dimethyl-Tyr-D-Met-Gly-N-methyl-Phe-DL-cis-3-aminocyclohexanecarboxylic Acid Methyl Ester. HCl (Isomer B)

The title compound (Isomer B) is prepared according to the method of Example 6 using 0.070 g (0.088 mmole) of the second eluted product pentapeptide from Example 25 in 1 ml of acetic acid, and 0.5 ml of 5.6 N HCl in dioxane. The solvent is removed by evaporation under a stream of nitrogen, and the partially dried residue is lyophilized, giving the title compound (Isomer B) as the dihydrate. Structure assignment, except D or L stereochemistry of the 2,6-dimethyltyrosine residue, is confirmed by NMR and elemental analysis (C,H,N,Cl).

CHART A

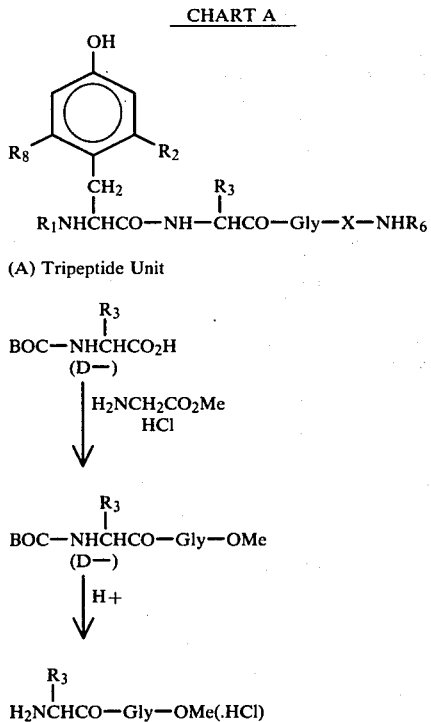

(A) Tripeptide Unit

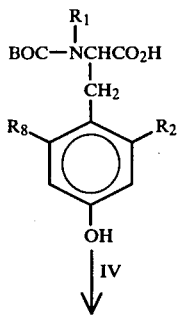

CHART B

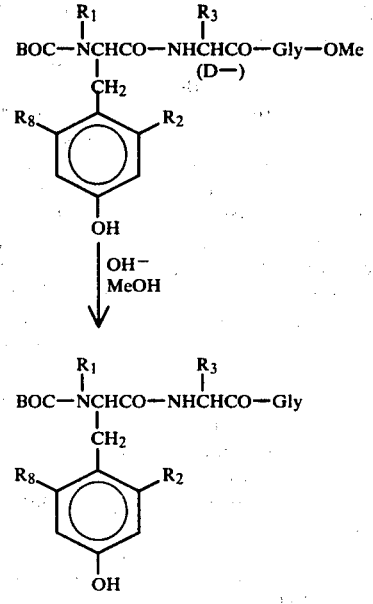

(B) Dipeptide Unit

CHART C

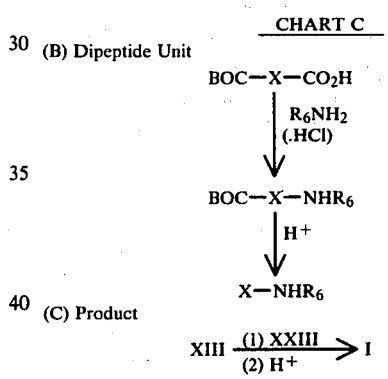

(C) Product

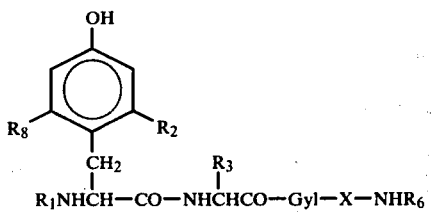

We claim:
1. A compound according to the formula wherein R₁ is:
(a) hydrogen; or
(b) alkyl of 1 to 6 carbon atoms, inclusive;
wherein R₂ and R₈ are:
(a) hydrogen; or
(b) alkyl of 1 to 6 carbon atoms, inclusive; R₂ and R₈ each being the same of different;
wherein R₃ is:
(a) alkylthioalkyl having 2 to 6 carbon atoms, inclusive;
(b) alkylsulfinylalkyl have 2 to 6 carbon atoms, inclusive;

wherein X is:

(a) 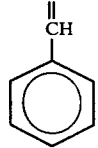  (b) 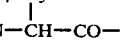

wherein R₄ is:
(a) hydrogen; or
(b) alkyl of 1 to 6 carbon atoms, inclusive;
wherein R₅ is:

(a) 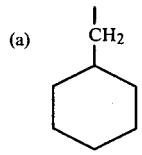  (b) 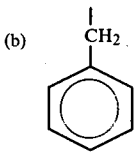  (c) 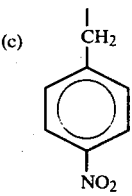

wherein R₆ is:
(a) cyclohexyl; substituted 2, 3 or 4 by R₇; or
(b) phenyl; substituted ortho, meta or para by R₇;
wherein R₇ is:
(a) hydrogen;

(b) alkyl ester of carboxylic acid of 1 to 6 carbon atoms, inclusive.
(c) hydroxyalkyl of 1 to 6 carbon atoms, inclusive; and the pharmaceutically acceptable salts.

2. A compound according to claim 1 wherein R₆ is phenyl; ortho, para, or meta substituted by R₇.

3. L-Tyrosyl-D-methionylglycyl-N-[3-(methoxycarbonyl)phenyl]-L-phenylalaninamide monohydrochloride, a compound according to claim 2.

4. N-Methyl-L-tyrosyl-D-methionylglycyl-N-[(3-hydroxymethyl)phenyl]-L-phenylalaninamide hydrochloride, a compound according to claim 2.

5. A compound according to claim 1 wherein R₆ is cyclohexyl, 2, 3 or 4 substituted by R₇.

6. L-Tyrosyl-D-methionylglycyl-N-[cis-3-(methoxycarbonyl)cyclohexyl]-L-phenylalaninamide monohydrochloride, a compound according to claim 5.

7. L-Tyrosyl-λ-(methylsulfinyl)-D-α-aminobutyrylglycyl-N-[cis-(3-methoxycarbonyl)cyclohexyl]-L-phenylalaninamide hydrochloride, a compound according to claim 5.

8. 2,6-Dimethyl-D-tyrosyl-D-methionylglycyl-N-[cis-(3-methoxycarbonyl)cyclohexyl]-N-methyl-L-phenylalaninamide hydrochloride, a compound according to claim 5.

9. 2,6-Dimethyl-L-Tyrosyl-D-methionylglycyl-N-[cis-(3-methoxycarbonyl)cyclohexyl]-Nᵅmethyl-L-phenylalaninamide hydrochloride, a compound according to claim 5.

* * * * *